United States Patent
Oka

(10) Patent No.: US 6,645,154 B2
(45) Date of Patent: Nov. 11, 2003

(54) BLOOD-PRESSURE-WAVEFORM MONITORING APPARATUS

(75) Inventor: Tohru Oka, Ichinomiya (JP)

(73) Assignee: Colin Corporation, Komaki (JP)

( * ) Notice: Subject to any disclaimer, the term of this patent is extended or adjusted under 35 U.S.C. 154(b) by 117 days.

(21) Appl. No.: 10/028,709

(22) Filed: Dec. 28, 2001

(65) Prior Publication Data

US 2002/0161305 A1 Oct. 31, 2002

(30) Foreign Application Priority Data

Apr. 27, 2001 (JP) ........................................ 2001-130765

(51) Int. Cl.$^7$ .............................................. A61B 05/00
(52) U.S. Cl. ...................................... 600/485; 600/500
(58) Field of Search ................................ 600/485, 490, 600/493–6, 500

(56) References Cited

U.S. PATENT DOCUMENTS

| | | | |
|---|---|---|---|
| 5,830,149 A | | 11/1998 | Oka et al. |
| 5,865,756 A | * | 2/1999 | Peel, III ................... 600/485 |
| 5,873,834 A | | 2/1999 | Yanagi et al. |
| 6,022,320 A | * | 2/2000 | Ogura et al. ................. 600/490 |
| 6,527,726 B2 | * | 3/2003 | Goto et al. .................. 600/485 |

FOREIGN PATENT DOCUMENTS

EP   0 829 227 A2   3/1998

* cited by examiner

Primary Examiner—Robert L. Nasser
(74) Attorney, Agent, or Firm—Oliff & Berridge, PLC

(57) ABSTRACT

An apparatus for monitoring a blood-pressure waveform representing a blood pressure of a living subject, including a cuff which is around a portion of the subject, a blood-pressure determining device which determines a blood pressure of the subject based on a signal obtained while a pressure in the cuff is changed, a blood-pressure-waveform detecting device which continuously detects the blood-pressure waveform, a display device which displays the blood-pressure waveform, a cuff-using-blood-pressure-measurement starting device for operating, when a prescribed blood-pressure-measurement-starting condition is satisfied, the blood-pressure determining device to determine the blood pressure of the subject, a pulse-wave detecting device which is adapted to be worn on a portion of the subject that is not located on a downstream side of the portion around which the cuff is wound, an estimated-blood-pressure-waveform determining device for continuously determining, based on the pulse wave detected by the pulse-wave detecting device, a estimated blood-pressure waveform representing an estimated blood pressure of the subject, according to a predetermined relationship between blood-pressure waveform and pulse wave, and a waveform-displaying control device for operating, when the blood-pressure waveform is not abnormal, the display device to display the blood-pressure waveform, and operating, when the blood-pressure waveform is abnormal, the display device to display the estimated blood-pressure waveform.

8 Claims, 9 Drawing Sheets

BLOOD-PRESSURE-WAVEFORM MONITORING APPARATUS

BACKGROUND OF THE INVENTION

1. Field of the Invention

The present invention relates to a blood-pressure-waveform monitoring apparatus which continuously displays a waveform representing blood pressure of a living subject.

2. Related Art Statement

During a surgical operation, or in an intensive care unit, a blood-pressure-waveform monitoring apparatus may be used to continuously monitor blood pressure of a patient. The blood-pressure-waveform monitoring apparatus includes a blood-pressure-waveform detecting device which continuously detects a blood-pressure waveform from the patient, and a display device which displays the blood-pressure waveform detected by the blood-pressure-waveform detecting device. The blood-pressure-waveform detecting device may be one which employs a tonometry in which a pressure-pulse-wave sensor is used to detect a blood-pressure waveform, or one which employs a catheter method in which a catheter is used to detect a blood-pressure waveform. In the tonometry, the pressure-pulse-wave sensor is fixed above an artery, such as a radial artery, that is considerably near to skin, and is pressed with an appropriate force against the artery via the skin to detect a pressure pulse wave that is produced by pulsation of the artery in synchronism with heartbeat of the patient. The thus detected pressure pulse wave represents relative change of blood pressure in the artery, and therefore represents a blood-pressure waveform. Meanwhile, the catheter-type pressure-waveform detecting device requires a person to invasively insert the catheter into an artery of the patient so that a pressure-converting element in the catheter can directly detect blood pressure in the artery.

Thus, the tonometry-type pressure-waveform detecting device can accurately measure relative change of the intraarterial blood pressure, but cannot accurately measure absolute blood pressure because of visco-elasticity of the skin or subcutaneous tissue located above the artery. Hence, it is needed to wind a cuff around an upper arm of the patient, measure a blood pressure of the upper arm of the patient using the cuff, and calibrate the relative change of intraarterial blood pressure based on the thus measured upper-arm blood pressure. This calibration is periodically performed since the pressure-pulse wave sensor may be moved out of position. In addition, when the blood pressure detected by the pressure-pulse-wave sensor is judged as being abnormal, a blood-pressure measurement using the cuff may be started to obtain a more reliable blood-pressure value. Meanwhile, the catheter-type pressure-waveform detecting device usually requires a person to insert the catheter into a considerably distal portion of a peripheral artery of a patient and, in an emergency, a cuff may be needed to be wound around an upper arm of the patient so as to obtain a central-side blood-pressure value of the patient.

As described above, in the continuous blood-pressure monitoring using the tonometry-type pressure-waveform detecting device, not only the pressure-pulse-wave sensor is worn on a patient, but also the cuff is worn on an upper arm of the patient. In many cases, concurrently with the continuous blood-pressure-waveform monitoring, the patient receives an intravenous drip. In those cases, however, the cuff or the pressure-pulse-wave sensor cannot be worn on the arm into which the drip tube is inserted, because, if the cuff presses the upper arm, the veins are occluded and the drops cannot smoothly flow into the veins, or because the pressure-pulse-wave sensor or the cords of the sensor interfere with the drip tube.

Thus, in many cases, the pressure-pulse-wave sensor is worn on the wrist of the arm around which the cuff is wound. In those cases in which the pressure-pulse-wave sensor and the cuff are worn on the same arm, the pressure-pulse-wave sensor that is located on the downstream side of the cuff cannot detect an accurate blood-pressure waveform during a blood-pressure measurement using the cuff. Therefore, the display device is stopped from displaying the inaccurate blood-pressure waveform, or otherwise is allowed to display the blood-pressure waveform having an abnormal shape. A blood-pressure measurement using the cuff may take more than one minute when an abnormally high blood pressure or an arrhythmia occurs to the patient. That is, although the blood-pressure-waveform monitoring apparatus is used in those cases in which it is medically needed to continuously monitor a blood-pressure waveform of a patient, each blood-pressure measurement using the cuff interrupts the continuous blood-pressure-waveform monitoring and thereby disadvantageously reduces the significance of use of the monitoring apparatus.

Likewise, the catheter-type blood-pressure-waveform monitoring apparatus requires, in many cases, the catheter and the cuff to be worn on the same arm of a patient. Therefore, like the tonometry-type blood-pressure-waveform monitoring apparatus, the catheter-type blood-pressure-waveform monitoring apparatus suffers the problem that each blood-pressure measurement using the cuff disadvantageously interrupts the continuous blood-pressure-waveform monitoring.

SUMMARY OF THE INVENTION

It is therefore an object of the present invention to provide a blood-pressure-waveform monitoring apparatus which can display an accurate blood-pressure waveform even during a blood-pressure measurement using a cuff.

The above object has been achieved by the present invention. According to the present invention, there is provided an apparatus for monitoring a blood-pressure waveform representing a blood pressure of a living subject, comprising an inflatable cuff which is adapted to be wound around a first portion of the subject; a blood-pressure determining device which determines a blood pressure of the subject based on a signal obtained while a pressure in the cuff is changed; a blood-pressure-waveform detecting device which is adapted to be worn on a second portion of the subject and continuously detects the blood-pressure waveform representing the blood pressure of the subject; a display device which displays the blood-pressure waveform detected by the blood-pressure-waveform detecting device; a cuff-using-blood-pressure-measurement starting means for operating, when a prescribed blood-pressure-measurement-starting condition is satisfied, the blood-pressure determining device to determine the blood pressure of the subject; a pulse-wave detecting device which is adapted to be worn on a third portion of the subject that is not located on a downstream side of the first portion around which the cuff is wound, and which detects a pulse wave from the third portion of the subject; an estimated-blood-pressure-waveform determining means for continuously determining, based on the pulse wave detected by the pulse-wave detecting device, an estimated blood-pressure waveform representing an estimated blood pressure of the subject, according to a predetermined relationship between blood-pressure waveform and pulse wave; and a waveform-displaying control means for operating, when the blood-pressure waveform detected by the blood-pressure-waveform-detecting device is not abnormal, the display device to display the blood-pressure waveform, and operating, when the blood-pressure waveform is abnormal, the display device to display the estimated blood-pressure waveform in place of the blood-pressure waveform.

Since the pulse-wave detecting device is worn on the portion of the subject that is not located on the downstream side of the portion around which the cuff is wound, the pulse wave detected by the pulse-wave detecting device is not influenced by the inflation of the cuff to press the portion around which the cuff is wound. Therefore, the estimated blood-pressure waveform determined by the estimated-blood-pressure-waveform determining means based on the pulse wave actually detected by the pulse-wave detecting device according to the predetermined relationship between blood-pressure waveform and pulse wave, is not influenced by the inflation of the cuff. On the other hand, if the pressure-waveform detecting device is worn on a portion of the subject that is located on the downstream side of the cuff, the blood-pressure waveform detected by the pressure-waveform detecting device becomes abnormal because of the inflation of the cuff. In this case, however, the waveform-displaying control means operates, when the blood-pressure waveform detected by the pressure-waveform detecting device is abnormal, the display device to display, in place of the blood-pressure waveform, the estimated blood-pressure waveform determined by the estimated-blood-pressure-waveform determining means. Thus, the present apparatus displays an accurate blood-pressure waveform even during each blood-pressure measurement using the cuff.

According to a preferred feature of the present invention, the pulse-wave detecting device comprises a photoelectric-pulse-wave detecting device which is adapted to be worn on the third portion of the subject, emits a light toward the third portion, and detects a photoelectric pulse wave from the third portion. The photoelectric-pulse-wave detecting device is small-sized and light-weighted. Therefore, even in the case where a drip tube is inserted in a blood vessel of a first arm of the subject that is different from the other or second arm of the subject on which the cuff is worn, the photoelectric-pulse-wave detecting device can be worn on the first arm, without interfering with the drip tube.

According to another preferred feature of the present invention, the waveform-displaying control means judges that the blood-pressure waveform is abnormal, when the pressure of the cuff is not lower than a prescribed lowest pressure at which the cuff would at least partly block a flow of blood through the first portion of the subject, and thereby operates the display device to display the estimated blood-pressure waveform. In the case where an estimated blood-pressure waveform is displayed when an abnormality of the blood-pressure waveform is found directly from the blood-pressure waveform itself, it may be difficult to find the abnormality of the blood-pressure waveform. However, according to this feature, when an abnormality of the blood-pressure waveform is caused by the inflation of the cuff, the estimated blood-pressure waveform is displayed with reliability in place of the blood-pressure waveform being abnormal.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
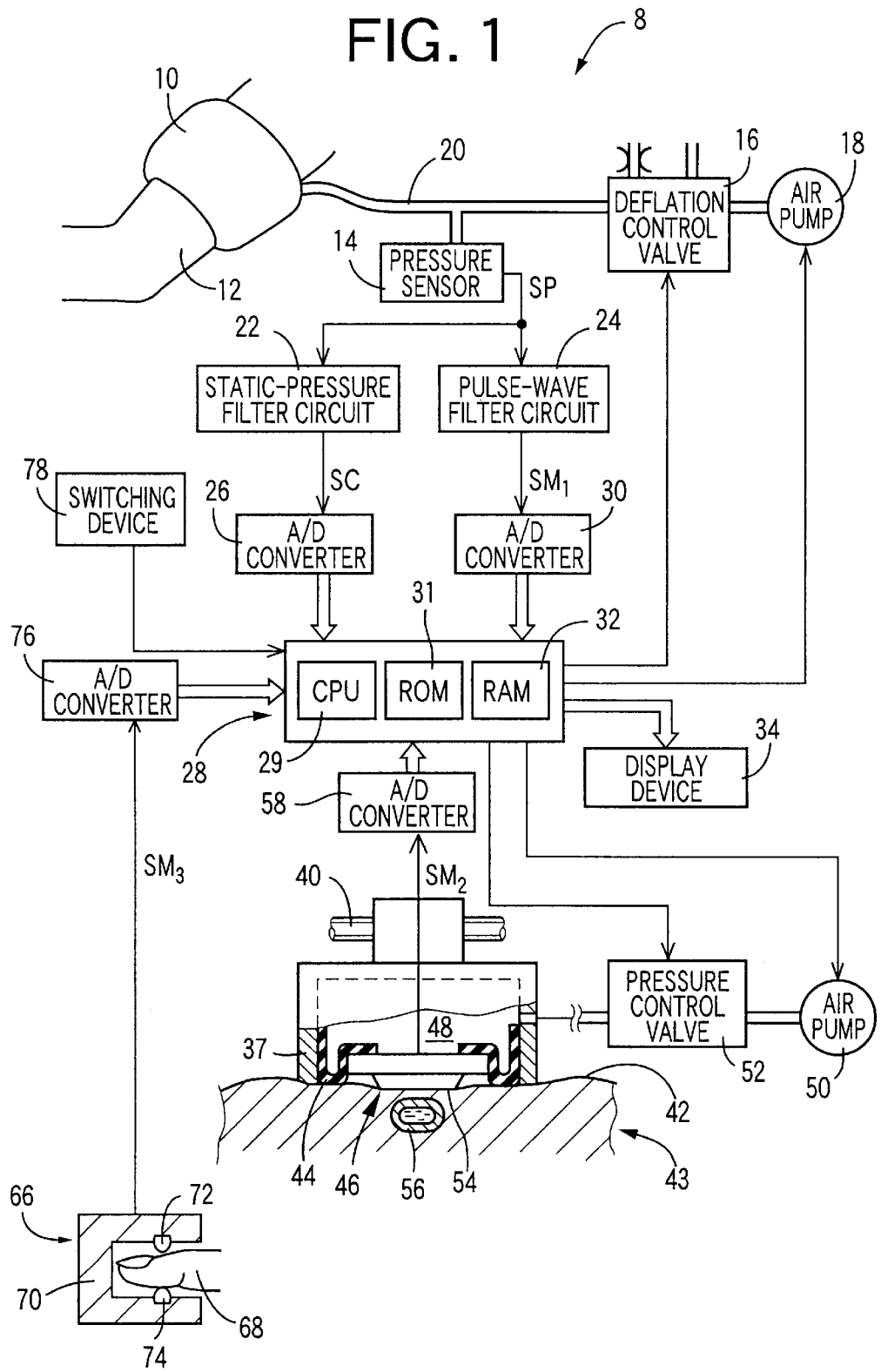
FIG. 1 is a diagrammatic view for explaining a construction of a blood-pressure-waveform monitoring apparatus to which the present invention is applied.

Hereinafter, there will be described an embodiment of the present invention in detail by reference to the drawings. FIG. 1 shows a diagrammatic view for explaining a construction of a blood-pressure-waveform monitoring apparatus 8 to which the present invention is applied.

In FIG. 1, reference numeral 10 designates an inflatable cuff which has a belt-like cloth bag and a rubber bag accommodated in the cloth bag and which is adapted to be wound around, e.g., a right upper arm 12 of a patient as a living subject. The cuff 10 is connected to a pressure sensor 14, a deflation control valve 16, and an air pump 18 via a piping 20. The deflation control valve 16 is selectively placed in a pressure-supply position in which the control valve 16 permits a pressurized air to be supplied from the air pump 18 to the cuff 10, a pressure-maintain position in which the control valve 16 maintains a pressure in the cuff 10; a slow-deflation position in which the control valve 16 permits the pressurized air to be slowly discharged from the cuff 10, and a quick-deflation position in which the control valve 16 permits the pressurized air to be quickly discharged from the cuff 10.

The pressure sensor 14 detects an air pressure $P_K$ in the cuff 10, and supplies a pressure signal SP representing the detected pressure $P_K$ to each of a static-pressure filter circuit 22 and a pulse-wave filter circuit 24. The static-pressure filter circuit 22 includes a low-pass filter and extracts, from the pressure signal SP, a static-pressure component contained in the signal SP, i.e., a cuff-pressure signal SC representing the static pressure in the cuff 10. The cuff-pressure signal SC is supplied to a control device 28 via an A/D (analog-to-digital) converter 26. The pulse-wave filter circuit 24 includes a band-pass filter and extracts, from the pressure signal SP, an oscillating component having predetermined frequencies, i.e., a cuff-pulse-wave signal $SM_1$. The cuff-pulse-wave signal $SM_1$ is supplied to the control device 28 via an A/D converter 30. The cuff-pulse-wave signal $SM_1$ represents a cuff pulse wave $W_K$, i.e., an oscillatory pressure wave which is produced from a brachial artery, not shown, of the patient in synchronism with the heartbeat of the patient and is propagated to the cuff 10.

The control device 28 is provided by a so-called microcomputer including a CPU (central processing unit) 29, a ROM (read only memory) 31, a RAM (random access memory) 32 and an I/O (input-and-output) port, not shown. The CPU 29 processes signals according to the control programs pre-stored in the ROM 31 by utilizing the temporary-storage function of the RAM 32, and supplies drive signals via the I/O port to respective drive circuits, not shown, associated with the deflation control valve 16 and the air pump 18 so as to control the pressure in the cuff 10 and determine, according to oscillometric method, a blood-pressure value BP of the patient, such as a systolic blood-pressure value $BP_{SYS}$ and/or a diastolic blood-pressure value $BP_{DIA}$, based on change of the cuff pulse wave $W_K$ represented by the cuff-pulse-wave signal $SM_1$. In addition, the CPU 29 operates a display device 34 to display the thus determined blood-pressure value BP. The display device 32 may include a cathode ray tube (CRT).

Figure 2:
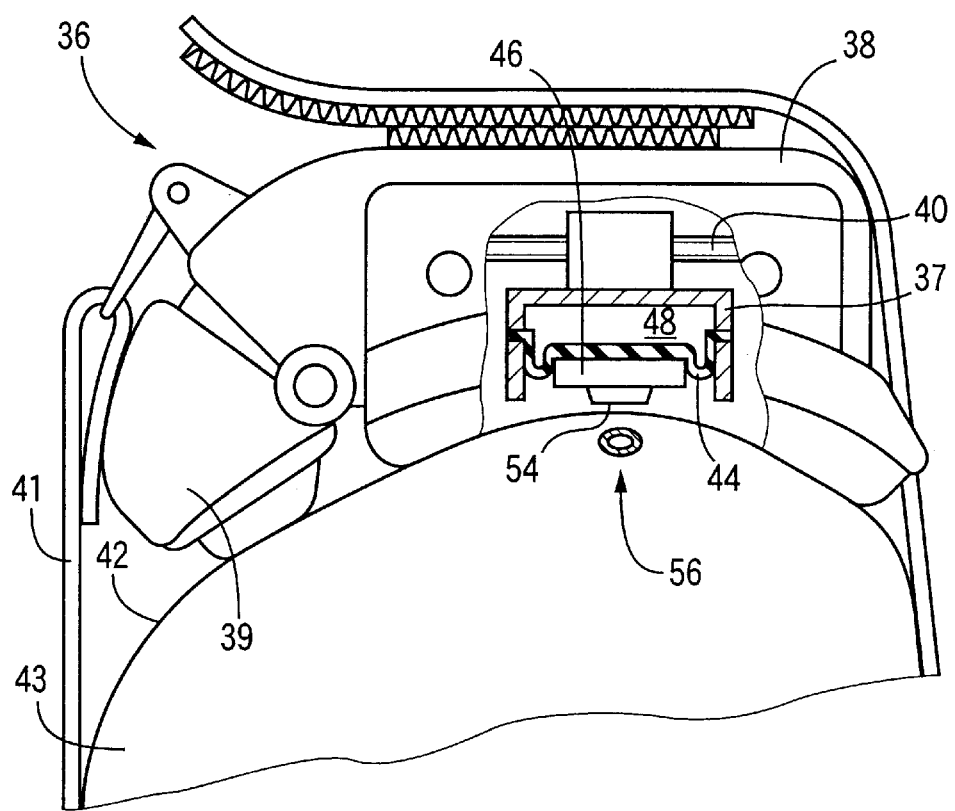
FIG. 2 is an enlarged view of a pressure-pulse-wave detecting probe of the apparatus of FIG. 1, a portion of the probe being cut away.

The monitoring apparatus 8 further includes a pressure-pulse-wave detecting probe 36 functioning as a continuous-blood-pressure-waveform detecting device. As shown in detail in FIG. 2, the pressure-pulse-wave detecting probe 36 includes a case 38 which accommodates a container-like sensor housing 37; and a feed screw 40 which is threadedly engaged with the sensor housing 37 and is rotated by an electric motor, not shown, provided in a drive section 39 of the case 38 so as to move the sensor housing 37 in a widthwise direction of a radial artery 56. With the help of a fastening band 41 which is connected to the case 38, the case 38 is detachably attached to a wrist 43 of the arm wound which the cuff 10 is wound, such that an open end of the sensor housing 37 is opposed to a body surface 42 of the wrist. In addition, the probe 36 includes a pressure-pulse-wave sensor 46 which is secured via a diaphragm 44 to an inner wall of the sensor housing 37, such that the sensor 46 is movable relative to the housing 37 and is advanceable out of the open end of the same 37. The sensor housing 37, the diaphragm 44, etc. cooperate with one another to define a pressure chamber 48, which is supplied with a pressurized air from an air pump 50 via a pressure-control valve 52 so that the pressure-pulse-wave sensor 46 is pressed against the body surface 42 with a pressing force $P_{HDP}$ corresponding to the air pressure in the pressure chamber 48. Thus, the pressing force $P_{HDP}$ applied to the sensor 46 is expressed in terms of the air pressure (mmHg) in the pressure chamber 48.

The sensor housing 37 and the diaphragm 44 cooperate with each other to provide a pressing device 62 which presses the pressure-pulse-wave sensor 46 against the radial artery 56, with an optimum pressing force $P_{HDPO}$, described later. The feed screw 40 and the not-shown motor cooperate with each other to provide a pressing-position changing device or a widthwise-direction moving device 64 which moves the pressure-pulse-wave sensor 46 in the widthwise direction of the radial artery 56 and thereby changes a pressing position where the sensor 46 is pressed.

The pressure-pulse-wave sensor 46 includes a semiconductor chip provided by, e.g., a monocrystalline silicon, and having a flat press surface 54, and a number of semiconductor pressure-sensing elements (not shown) arranged on the press surface 54 at a regular interval of about 0.2 mm in the widthwise direction of the radial artery 56 (i.e., the direction of movement of the sensor 46 parallel to the feed screw 40). The sensor 46 is pressed against the body surface 42 of the wrist 43 right above the radial artery 56, to detect a pressure pulse wave PW, i.e., an oscillatory pressure wave which is produced from the radial artery 56 and is propagated to the body surface 42, and supplies a pressure-pulse-wave signal $SM_2$ representing the detected pressure pulse wave PW, to the control device 28 via an A/D converter 58.

The CPU 29 of the control device 28 processes signals according to the control programs pre-stored in the ROM 31 by utilizing the temporary-storage-function of the RAM 32, and supplies drive signals to respective drive circuits, not shown, associated with the pressure control valve 52 and the air pump 50 so as to control the pressure in the pressure chamber 48. In addition, the control device 28 determines, based on the pressure pulse wave PW continuously detected by the pressure-pulse-wave sensor 46 while the pressure in the pressure chamber 48 is slowly changed, an optimum pressing pressure $P_{HDPO}$ at which the sensor 46 is optimally pressed against the radial artery 56 such that a portion of the wall of the artery 56 is substantially flattened. The control device 28 controls the pressure control valve 52 so as to maintain the pressure of the pressure chamber 48 at the thus determined optimum pressing pressure $P_{HDPO}$.

The monitoring apparatus 8 further includes a photoelectric-pulse-wave detecting device 66 functioning as a pulse-wave detecting device. The detecting device 66 detects a photoelectric pulse LW wave representing change of volume of blood present in peripheral blood vessels of the patient. In the present embodiment, the detecting device 66 is worn on an end portion of a finger of the other arm than the arm around which the cuff 10 is wound. The photoelectric-pulse-wave detecting device 66 has the same construction as that of a known device used to detect pulse rate. More specifically described, the detecting device 66 includes a housing 70 that can accommodate the end portion of finger; a light emitting element 72 as a light source that is disposed on one of opposite walls of the housing 70 and emits, toward the skin of the patient, a red or infrared light in a frequency range that is reflected by hemoglobin (preferably, a light having a wavelength of about 800 nm, that is not influenced by oxygen saturation); and a light receiving element 74 that is disposed on the other wall of the housing 72 such that the light receiving element 74 is opposed to the light emitting element 72, and detects the light transmitted through the end portion 68 of finger. The light receiving element 74 continuously produces a photoelectric-pulse-wave signal $SM_3$ representing the detected intensity of light, i.e., volume of blood present in capillaries of the end portion of finger, and supplies the photoelectric-pulse-wave signal $SM_3$ to the control device 28 via an A/D converter 76.

A switching device 78 is manually operable by an operator to supply, to the control device 28, a switch signal to switch the present monitoring apparatus 8 into a control mode in which the control device 28 carries out a control operation that will be described in detail, later, but, in short, the control device 28 judges whether the pressure pulse wave PW is abnormal and, if a positive judgment is made, operates the display device 34 to display an estimated-blood-pressure waveform EPW in place of the abnormal pressure pulse wave PW. In the case where the operator cannot help wearing the pressure-pulse-wave detecting probe 36 on the arm around which the cuff 10 is wound, the operator needs to operate the switching device 78 to supply the switch signal to the control device 28.

Figure 3:
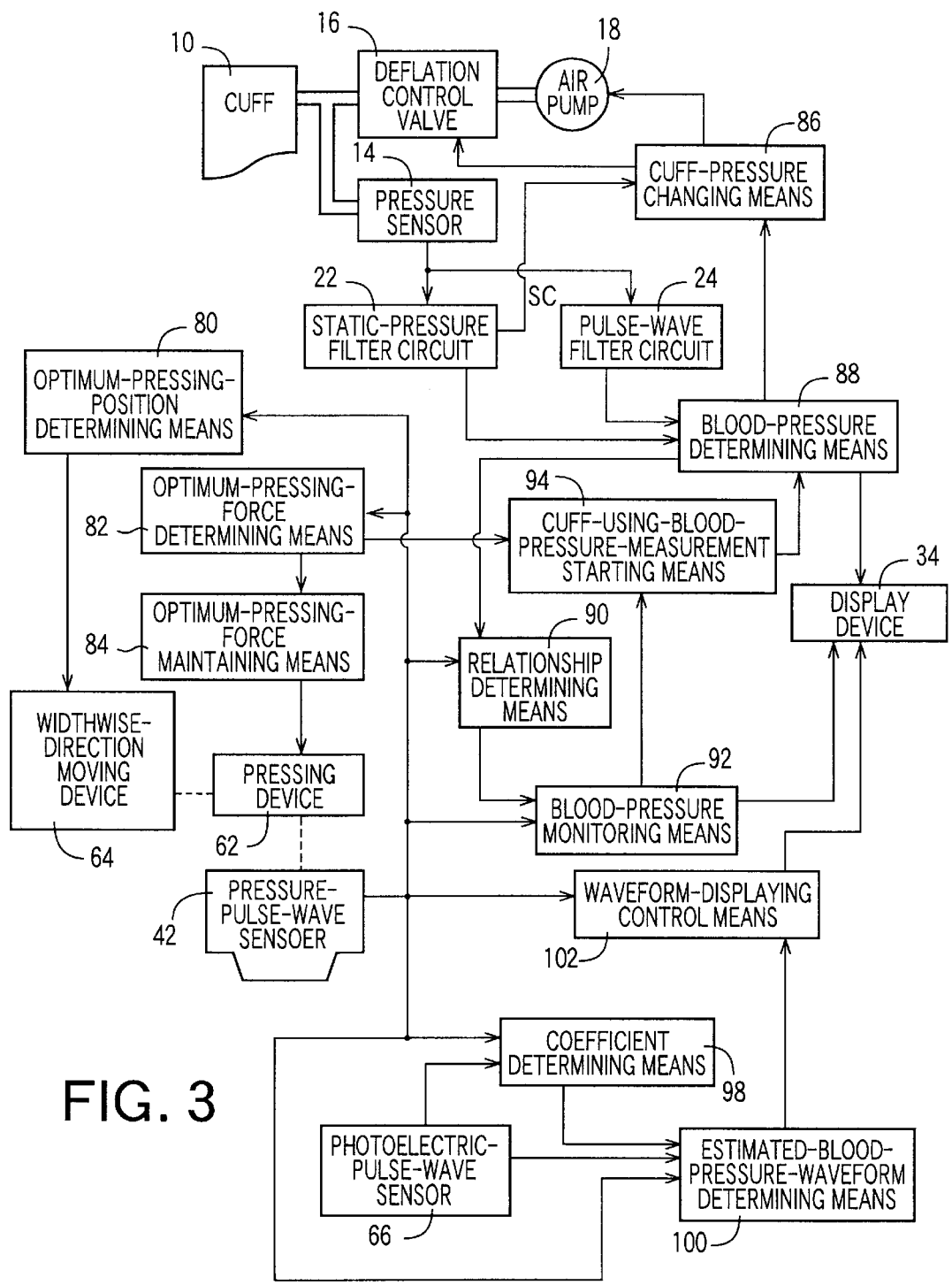
FIG. 3 is a block diagram for explaining essential control functions of a control device of the apparatus of FIG. 1.

FIG. 3 is a block diagram for explaining essential control functions of the control device 28. In the figure, an optimum-pressing-position determining means 80 operates when a prescribed pressing-position changing condition (i.e., an APS-starting condition) is satisfied, for example, when the pressure-pulse-wave detecting probe 36 is initially worn on the patient, or when the pressure-pulse-wave sensor 46 is largely moved relative to the radial artery 56 so that one of the pressure-sensing elements of the sensor 46 that detects the greatest one of the respective amplitudes of heartbeat-synchronous pulses detected by all the pressure-sensing elements is located in one of prescribed opposite end portions of the array of pressure-sensing elements. When the APS-starting condition is satisfied, first, the determining means 80 operates the pressing device 62 to press the pressure-pulse-wave sensor 46 at a first prescribed pressing pressure $P_1$ which would be sufficiently lower than an optimum pressing pressure $P_{HDPO}$ and, in this state, judges whether the one pressure-sensing element that detects the greatest amplitude is located in a prescribed middle range of the array of pressure-sensing elements. If a negative judgment is made, that is, if the one pressure-sensing element that detects the greatest amplitude is not positioned in the middle range, then the determining means 80 operates the pressing device 62 to move the sensor 46 away from the body surface 42 and operates the moving device 64, and again performs the above-described pressing and judging operations. Meanwhile, if a positive judgment is made indicating that the sensor 46 is positioned at an optimum pressing position, the determining means 80 determines the pressure-sensing element detecting the greatest amplitude, as a middle pressure-sensing element (i.e., an active element), and stores data indicating the pressure-sensing element determined as the active element. Then, the determining means 80 allows an optimum-pressing-force determining means 82 to operate.

Figure 4:
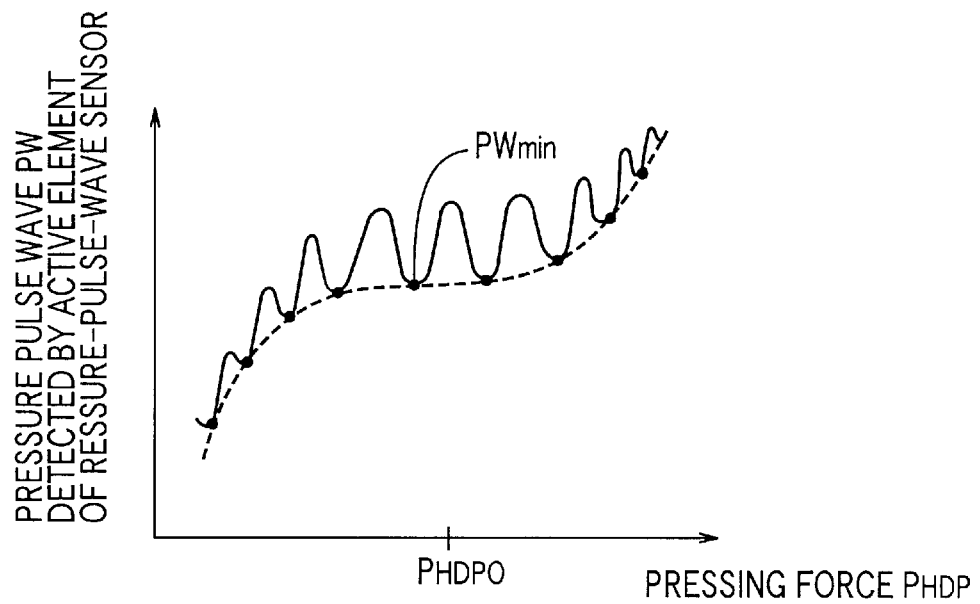
FIG. 4 is a graph for explaining a manner in which an optimum pressing force is determined by an optimum-pressing-force determining means shown in FIG. 3.

The optimum-pressing-force determining means 82 continuously changes the pressing pressure $P_{HDP}$ applied to the pressure-pulse-wave sensor 46 positioned at the optimum pressing position by the optimum-pressing-position determining means 80, and determines an optimum pressing pressure $P_{DHPO}$ based on the pressure pulse wave PW detected by the active element of the sensor 46. The optimum pressing pressure $P_{DHPO}$ may be determined as follows: First, as shown in a two-dimensional graph shown in FIG. 4, respective minimal values $PW_{min}$ of respective heartbeat-synchronous pulses of the pressure pulse wave PW detected by the active element of the sensor 46 when the pressing pressure $P_{HDP}$ is continuously increased in a pressure range which would include the optimum pressing pressure $P_{DHPO}$, are determined, and then a curve (indicated at broken line in FIG. 4) connecting the respective minimal values $PW_{min}$ of the pressure pulse wave PW is determined. Further, the optimum pressing pressure $P_{DHPO}$ is determined as a pressure which falls within a pressure range which has a prescribed width and whose middle pressure is equal to a middle pressure of a pressure range in which the thus determined curve is substantially horizontal. If the radial artery 56 is pressed by the sensor 46 with the pressure falling within the latter pressure range, a portion of the wall of the artery 56 that is pressed by the sensor 46 is so deformed as to be substantially flat.

Figure 5:
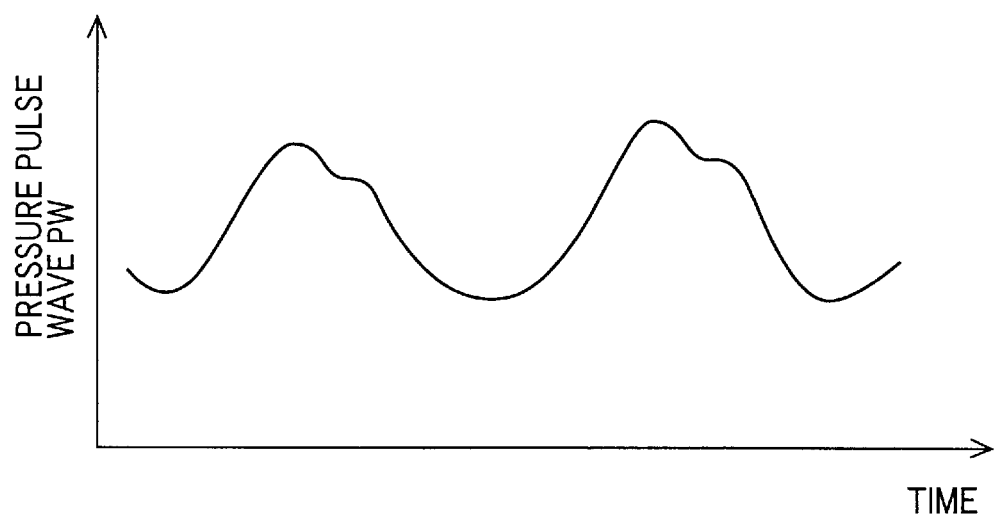
FIG. 5 is a graph showing an example of a pressure pulse wave PW(t) that is continuously detected by a pressure-pulse-wave sensor in a state in which a pressing force $P_{HDP}$ applied to the pressure-pulse-wave sensor is held at the optimum pressing force $P_{HDPO}$.

An optimum-pressing-force maintaining means 84 operates the air pump 50 and the pressure control valve 52 to maintain the pressing pressure $P_{HDP}$ applied by the pressing device 62 to the pressure-pulse-wave sensor 46, at the optimum pressing pressure $P_{HDPO}$ determined by the optimum-pressing-force determining means 82. FIG. 5 shows two heartbeat-synchronous pulses of a pressure pulse wave PW that are successively detected by the active element of the pressure-pulse-wave sensor 46 in the state in which the pressing pressure $P_{HDP}$ applied to the sensor 46 is maintained at the optimum pressing pressure $P_{HDPO}$. The pressure pulse wave PW shown in FIG. 5 is displayed on the display device 34 by a waveform-displaying control means 102, described later.

A cuff-pressure changing-means 86 operates the air pump 18 and the deflation control valve 16, based on the cuff-pressure signal SC supplied from the static-pressure filter circuit 22. Based on the cuff-pressure signal SC, the changing means 86 operates the air pump 18 and the control valve 16 to quickly increase a pressing pressure of the cuff 10, i.e., a cuff pressure Pc up to a prescribed target pressure $P_{CM}$ (e.g., 180 mmHg) which would be higher than a systolic blood-pressure value $BP_{SYS}$ of the patient and subsequently slowly decrease the cuff pressure Pc at a rate of from 2 to 3 mmHg/sec. After a blood-pressure determining means 88, described below, determines a blood pressure BP of the patient, the changing means 86 quickly decreases the cuff pressure Pc down to an atmospheric pressure.

A blood-pressure determining means 88 determines a systolic blood-pressure value $BP_{SYS}$, a mean blood-pressure value $BP_{MEAN}$, and a diastolic blood-pressure value $BP_{DIA}$ of the patient, based on the change of the cuff-pulse-wave signal SM, obtained while the pressure of the cuff 10 is slowly decreased by the cuff-pressure changing means 86, according to well-known oscillometric method. In addition, the determining means 88 operates the display device 34 to display the thus determined blood-pressure values $BP_{SYS}$, etc.

Figure 6:
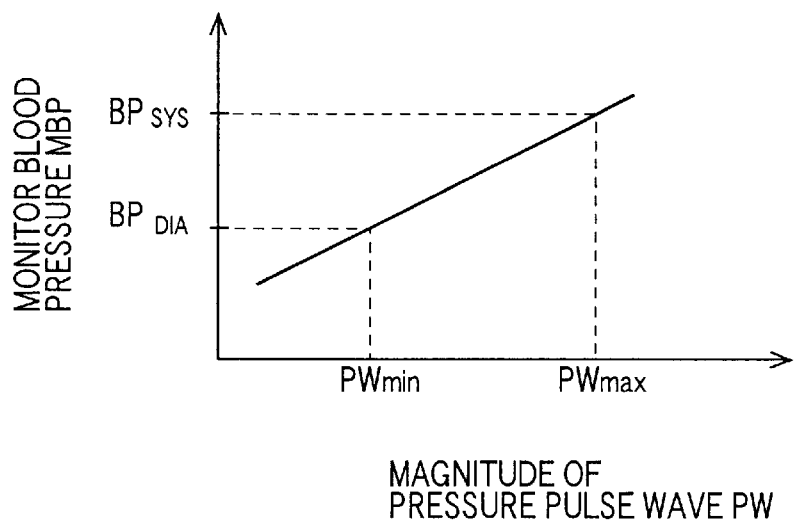
FIG. 6 is a graph showing an example of a relationship determined by a relationship determining means shown in FIG. 3.

A relationship determining means 90 determines, in advance, a relationship between blood pressure and magnitude of pressure pulse wave, based on the blood-pressure values BP determined by the blood-pressure determining means 88 and magnitudes of the pressure pulse wave PW detected by the active element of the pressure-pulse-wave sensor 46, i.e., the selected one of the pressure-sensing elements provided in the press surface 54. FIG. 6 shows an example of the relationship between blood pressure and magnitude of pressure pulse wave. In FIG. 6, symbols $PW_{min}$, $PW_{max}$ indicate a minimal magnitude (i.e., a magnitude of a rising point) and a maximal magnitude (i.e., a magnitude of a peak point) of a heartbeat-synchronous pulse of the pressure pulse wave PW, respectively.

A blood-pressure monitoring means 92 successively determines, according to the relationship between blood pressure and magnitude of pressure pulse wave, determined by the relationship determining means 90, a monitor blood pressure MBP of the patient based on a magnitude of each of respective heartbeat-synchronous pulses of the pressure pulse wave PW detected by the active element of the pressure-pulse-wave sensor 46. In addition, the monitoring means 92 operates the display device 34 to display the thus determined monitor blood-pressure values MBP.

A cuff-using-blood-pressure-measurement starting means 94 starts the blood-pressure determining means 88 to obtain, using the cuff 10, a highly reliable blood-pressure value BP, when a prescribed blood-pressure-measurement-starting condition is satisfied, for example, when a prescribed calibration period Tc of from ten and several minutes to several tens of minutes has elapsed after the last blood-pressure measurement is carried out by the blood-pressure determining means 88, when the optimum-pressing-force determining means 82 has updated the optimum pressing force $P_{HDPO}$, or when one of the monitor blood-pressure values MBP determined by the blood-pressure monitoring means 92 does not fall within a prescribed normal range.

A coefficient determining means 98 iteratively determines coefficients of an expression representing a relationship R between pressure pulse wave PW and photoelectric pulse wave LW, i.e., a relationship R used to determine pressure pulse wave PW based on photoelectric pulse wave LW. For example, the relationship R may be represented by the following Expression 1 based on an ARX (AutoRegressive eXogenous) model:

$$LW(t)+a_1LW(t-1)+\ldots+a_{na}LW(t-na)=b_1PW(t-1)+b_2PW(t-2)+\ldots+b_{nb}LW(t-nb) \quad \text{(Expression 1)}$$

In Expression 1, parameter "t" indicates time; and "LW(t)" and "PW(t)" indicates respective sampling data of photoelectric pulse wave and pressure pulse wave PW that are successively obtained at a sampling period. In addition, "na" and "nb" are sampling degrees that are experimentally determined, in advance, for example, (na, nb)=(4, 6) or (10, 10).

Expression 1 can be rewritten into the following Expression 2, by expressing the left-hand side of Expression 1 using a time shift operator q:

$$(1+a_1q^{-1}+\ldots+a_{na}q^{-na})LW(t)=b_1PW(t-1)+b_2PW(t-2)+\ldots+b_{nb}LW(t-nb) \quad \text{(Expression 2)}$$

And, Expression 2 can be rewritten into the following Expression 3, by expressing the right-hand side of Expression 2 using the time shift operator q:

$$(1+a_1q^{-1}+\ldots+a_{na}q^{-na})LW(t)=(b_1+b_2q^{-1}+\ldots+b_{nb}q^{-nb+1})PW(t-1) \quad \text{(Expression 3)}$$

Expression 3 can be rewritten into the following Expression 4:

$$PW(t-1)=\{(1+a_1q^{-1})/(b_1+b_2q^{-1}+\ldots+b_{nb}q^{-nb+1})\}\times LW(t) \quad \text{(Expression 4)}$$

Expression 4 can be rewritten into the following Expression 5:

$$PW(t-1)=\{A(q)/B'(q)\}\times LW(t) \quad \text{(Expression 5)}$$

In Expression 5, "B'(q)" is a function that is obtained by shifting "B(q)".

In the case where the relationship R represented by Expression 5 is employed, the coefficient determining means 98 determines coefficients $a_1, \ldots, a_{na}, b_1, \ldots, b_{nb}$ of Expression 5 (or Expression 4). Those coefficients $a_1, \ldots, a_{na}, b_1, \ldots, b_{nb}$ are determined by first obtaining an equation by replacing LW(t), LW(t−1), . . . , LW(t−na), PW(t−1), PW(t−2), . . . , PW(t−nb) of Expression 1 with respective magnitudes of photoelectric pulse wave LW and pressure pulse wave PW that are successively detected, repeating this calculation and thereby obtaining not less than the same number of equations as the total number (i.e., na+nb) of the coefficients, and resolving those simultaneous equations.

An estimated-blood-pressure-waveform determining means 100 successively determines, as an estimated magnitude of pressure pulse wave PW(t−1), an estimated blood pressure EPW(t−1) by replacing LW(t) of the right-hand side of Expression 5 whose coefficients have been determined by the coefficient determining means 98, with each magnitude of photoelectric pulse wave LW(t) actually detected by the photoelectric-pulse-wave detecting device 66.

The relationship R may change depending upon the condition of the patient. Therefore, it is preferred that the estimated-blood-pressure-waveform determining means 100 use the relationship R defined by the coefficients last determined by the coefficient determining means 98. However, since the pressure pulse wave PW(t) becomes abnormal when the upper arm 12 is pressed by the cuff 10, the coefficients determined while the upper arm 12 is pressed by the cuff 10 are not used. Thus, the estimated-blood-pressure-waveform determining means 100 use the relationship R defined by preferably the coefficients determined based on the normal pressure pulse wave PW(t), more preferably, the coefficients last determined based on the normal pressure pulse wave PW(t). Meanwhile, the estimated blood-pressure waveform EPW(t) is determined based on the photoelectric pulse wave LW(t) detected by the photoelectric-pulse-wave detecting device 66, and the photoelectric-pulse-wave detecting device 66 is not worn on the portion of the subject that is not located on the directly downstream side of the cuff 10. Therefore, though the upper arm 12 is pressed by the cuff 10, the estimated blood-pressure waveform EPW(t) corresponds to a pressure pulse wave PW(t) that would be detected by the pressure-pulse-wave sensor 46 if the upper arm 12 would not be pressed by the cuff 10.

A waveform-displaying control means 102 operates, when the pressure pulse wave PW(t) detected by the pressure-pulse-wave sensor 46 is not abnormal, the display device 34 to display the pressure pulse wave PW(t). Preferably, the display device 34 displays the pressure pulse wave PW(t) that has been converted into the monitor blood pressure MBP according to the relationship shown in FIG. 6. On the other hand, when the pressure pulse wave PW(t) is abnormal, the waveform-displaying control means 102 operates the display device 34 to display, in place of the pressure pulse wave PW(t), the estimated blood-pressure waveform determined by the estimated-blood-pressure waveform determining means 100. The abnormality of the pressure pulse wave PW(t) is found when an amplitude of a heartbeat-synchronous pulse of the pressure pulse wave PW(t) (i.e., a difference between a maximal magnitude PWmax and a minimal magnitude of the heartbeat-synchronous pulse) becomes smaller than a prescribed value while the blood-pressure determining means 88 is carried out and the upper arm 12 is pressed by the cuff 10, or when a shape or form of the pressure pulse wave PW(t) is abnormally deformed. Alternatively, the abnormality of the pressure pulse wave PW(t) may be found when the pressure of the cuff 10 is not lower than a prescribed pressure (e.g., 30 mmHg) at which the cuff 10 starts blocking the blood flow in the upper arm 12.

Figure 7:
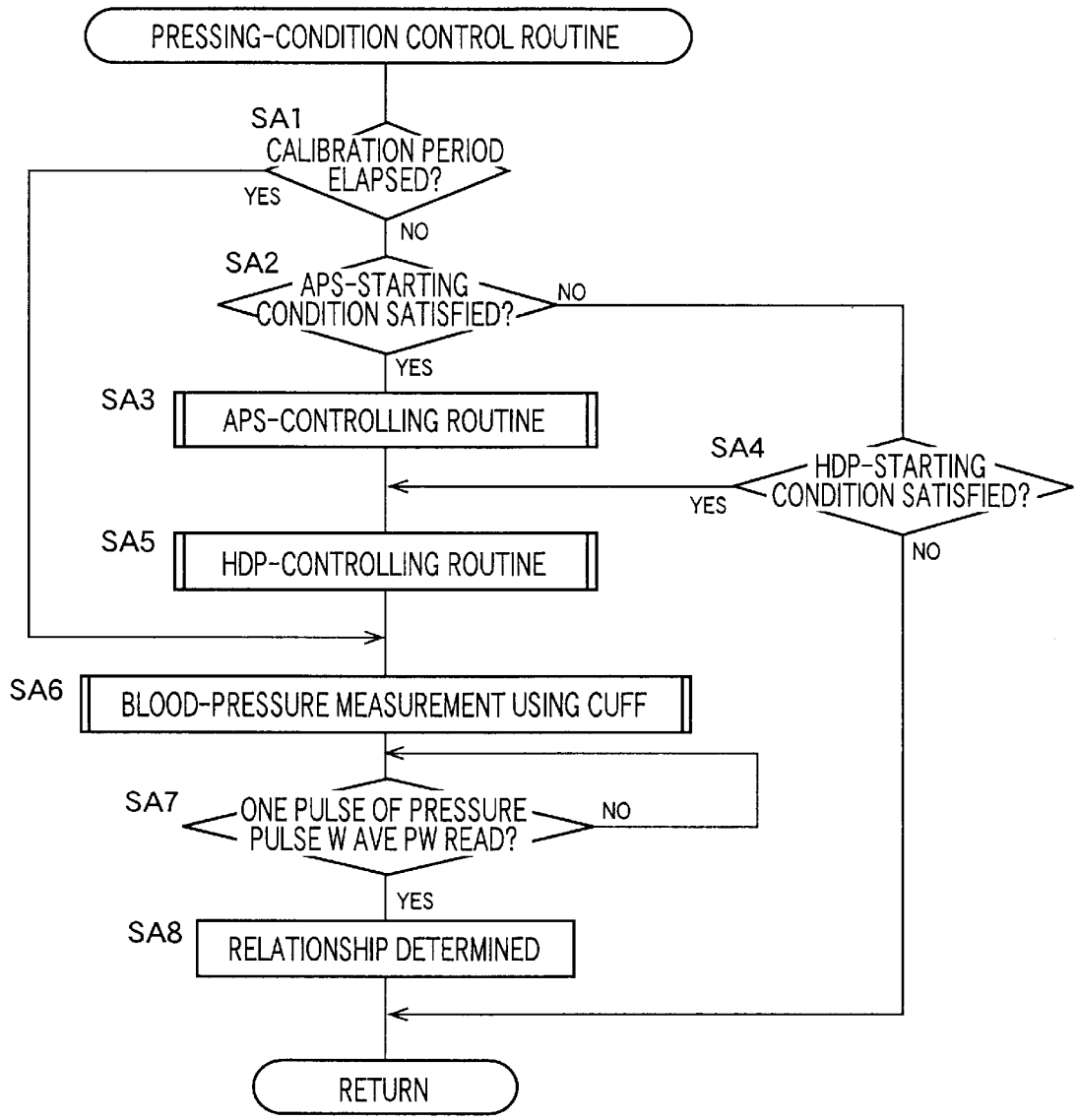
FIG. 7 is a flow chart representing a pressing-condition control routine according to which the control device shown in FIG. 1 controls a condition under which the pressure-pulse-wave sensor is pressed, such that the sensor is pressed at the optimum pressing position and with the optimum pressing force $P_{HDPO}$.
Figure 8:
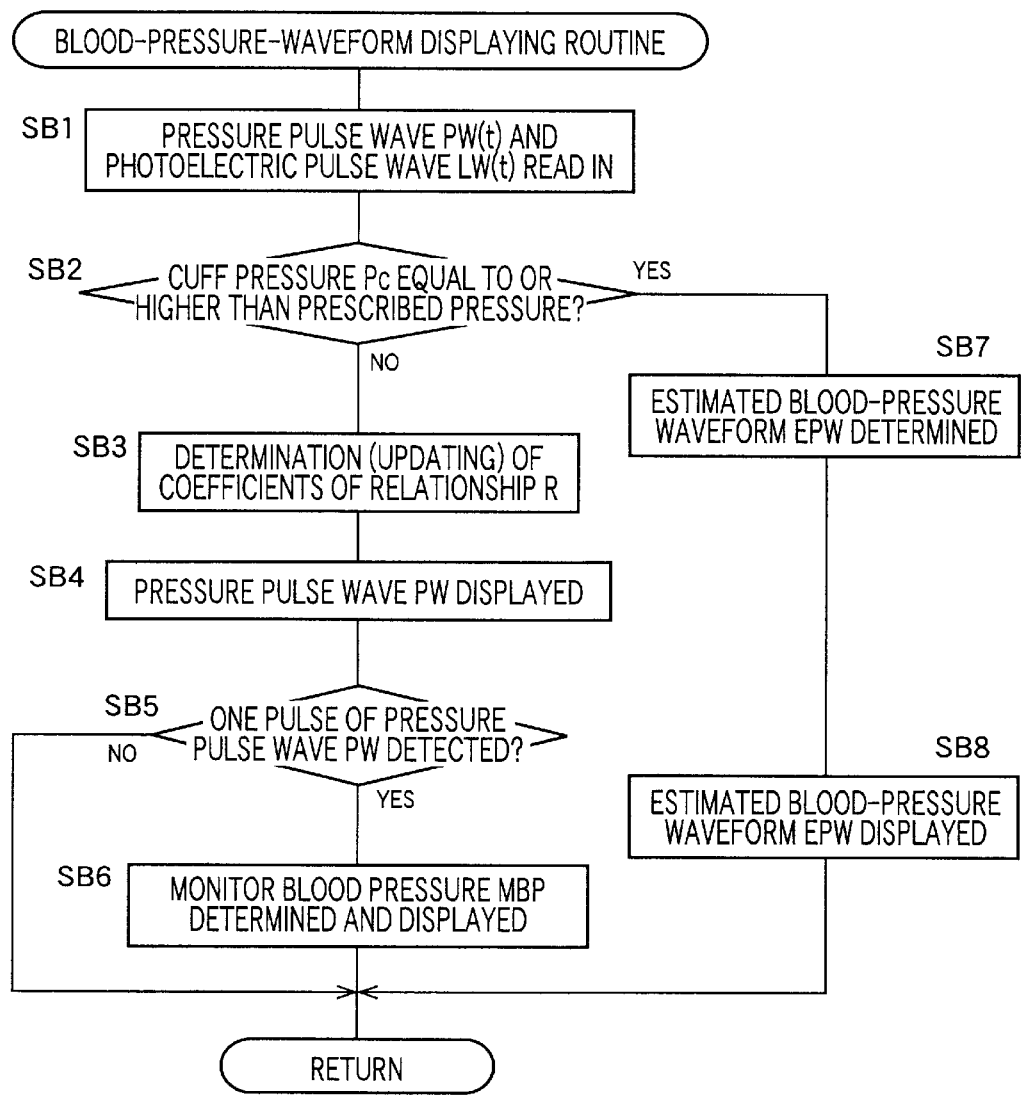
FIG. 8 is a flow chart representing a blood-pressure-waveform displaying routine according to which the control device shown in FIG. 1 operates for continuously displaying the pressure pulse wave PW(t) or a photoelectric pulse wave LW(t)

FIGS. 7 and 8 are flow charts representing essential control functions of the control device 28. FIG. 7 shows a flow chart representing a pressing-condition control routine according to which the control device 28 controls a condition under which the pressure-pulse-wave sensor 46 is pressed, such that the sensor 46 is pressed at the optimum pressing position and with the optimum pressing force $P_{HDPO}$, and FIG. 8 shows a flow chart representing a blood-pressure-waveform displaying routine according to which the control device 28 operates for continuously displaying a pressure pulse wave PW(t) or a photoelectric pulse wave LW (t). The blood-pressure-waveform displaying routine of FIG. 8 is carried out by time sharing or interrupt handling, independent of the pressing-condition control routine of FIG. 7.

According to the pressing-condition control routine of FIG. 7, first, the control device carries out Step SA1 (hereinafter, "Step" is omitted, if appropriate) corresponding to the cuff-using-blood-pressure-measurement starting means 94. At SA1, the control device judges whether a prescribed calibration period Tc of from ten and several minutes to several tens of minutes has elapsed after the relationship between blood pressure and magnitude of pressure pulse wave is last updated at SA8. Usually, a negative judgment is made at SA1, and the control goes to SA2 to judge whether a prescribed pressing-position changing condition (i.e., a APS-starting condition) has been satisfied, for example, whether one of the pressure-sensing elements, arranged on the press surface 54 of the pressure-pulse-wave sensor 46, that detects the greatest one of the respective amplitudes of the respective pressure pulse waves detected by all the elements is located in either one of the opposite end portions of the array of elements.

If the pressing position where the pressure-pulse-wave sensor 46 is pressed against the radial artery 56 is not appropriate, for example, when the pressure-pulse-wave detecting probe 36 is initially worn on the patient, and accordingly if the prescribed pressing-position changing condition is satisfied, a positive judgment is made at SA2, so that the control proceeds with SA3, i.e., an APS-controlling routine. According to this APS-controlling routine, the control device determines an optimum pressing position where one of the pressure-sensing elements that is located at substantially the middle of the array of elements detects the greatest one of the respective amplitudes of the respective pressure pulse waves detected by all the elements, that is, where one of the pressure-sensing elements that detects the greatest one of the respective amplitudes of the respective pressure pulse waves detected by all the elements, is located at substantially the middle of the array of elements. In addition, the control device determines, as an active element, the one pressure-sensing element located at substantially the middle of the array of elements. Since at SA2 and SA3 the pressing position where the pressure-pulse-wave sensor 46 is pressed is determined, SA2 and SA3 correspond to the optimum-pressing-position determining means 80.

On the other hand, if a negative judgment is made at SA2 because the pressure-pulse-wave sensor 46 is appropriately positioned relative to the radial artery 56, the control goes to SA4 to judge whether an optimum-pressing-force-determination starting condition (i.e., an HDP-starting condition) has been satisfied. This condition is satisfied, for example, when such a physical motion of the patient that changes the condition under which the pressure-pulse-wave sensor 46 is pressed and thereby changes the relationship determined at SA7, or when one of the monitor blood-pressure values MBP has largely changed from the last blood-pressure value BP measured using the cuff 10.

If the condition under which the pressure-pulse-wave sensor 46 is pressed has not changed, a negative judgment is made at SA4, the control goes back to SA1 and the following steps. On the other hand, if a positive judgment is made at SA4, or after the APS-controlling routine is carried out at SA3, the control goes to SA5, i.e., an HDP-controlling routine corresponding to the optimum-pressing-force determining means 82 and the optimum-pressing-force maintaining means 84.

More specifically described, the control device continuously increases the pressing force $P_{HDP}$ applied to the pressure-pulse-wave sensor 46, and determines, as an optimum pressing force $P_{HDPO}$, a value of the pressing force $P_{HDP}$ at the time when the active element of the sensor 46, positioned right above the radial artery 56, detects the greatest one of respective amplitudes of respective heartbeat-synchronous pulses of the pressure pulse wave PW(t), and replaces the prior optimum pressing force with the thus determined new optimum pressing force $P_{HDPO}$. Then, the pressing force $P_{HDP}$ applied to the sensor 46 is maintained at the new optimum pressing force $P_{HDPO}$. In the state in which the pressure-pulse-wave sensor 46 is pressed with the new optimum pressing force $P_{HDPO}$, the control device carries out SA6 and the following steps.

If a positive judgment is made at SA1 because the prescribed calibration period Tc has elapsed after the last determination of the relationship at SA7, or after the HDP-controlling routine is carried out at SA5, the control goes to SA6 corresponding to the cuff-pressure changing means 86 and the blood-pressure determining means 88. At SA6, the control device switches the deflation control valve 16 to its pressure-supply position, and operates the air pump 18, so that the pressure in the cuff 10 is quickly increased up to a prescribed target pressure (e.g., 180 mmHg) that would be higher than an expected systolic blood pressure of the patient. Then, the control device stops the air pump 18 and switches the deflation control valve 16 to its slow-deflation position, so that the pressure in the cuff 10 is slowly decreased at a prescribed rate of 3 mmHg/sec. In addition, the control device determines a systolic blood-pressure value $BP_{SYS}$, a mean blood-pressure value $BP_{MEAN}$, and a diastolic blood-pressure value $BP_{DIA}$ of the patient, based on the change of respective amplitudes of respective heartbeat-synchronous pulses of the cuff pulse wave $W_K$ represented by the cuff-pulse-wave signal $SM_1$ continuously obtained during the slow decreasing of the cuff pressure Pc, according to well-known oscillometric-type blood-pressure determining algorithm. The thus determined blood-pressure values BP are displayed on the display device 34. Then, the control device switches the deflation control valve 16 to its quick-deflation position, so that the pressure in the cuff 10 is quickly released.

Then, at SA7, the control device judges whether the control device has read in a length of the pressure pulse wave PW(t) that corresponds to one heartbeat of the patient. If a negative judgment is made at SA7, SA7 is repeated. If a positive judgment is made at SA7, then the control goes to SA8 corresponding to the relationship determining means 90.

At SA8, the control device determines or updates the relationship between blood pressure and magnitude of pressure pulse wave (i.e., the relationship shown in FIG. 6), based on a minimal magnitude $PW_{min}$ and a maximal magnitude $PW_{max}$ of the one heartbeat-synchronous pulse of the pressure pulse wave PW(t) detected by the active element of the pressure-pulse-wave sensor 46 and read in at SA7, and the diastolic and systolic blood-pressure values $BP_{DIA}$, $BP_{SYS}$ determined at SA6. After SA8, the control goes back to SA1 and the following steps.

Next, the blood-pressure-waveform displaying routine of FIG. 8 will be described. First, at SB1, the control device reads in the pressure-pulse-wave signal $SM_2$ (i.e., the pressure pulse wave PW(t)) supplied from the pressure-pulse-wave sensor 46 and the photoelectric-pulse-wave signal $SM_3$ (i.e., the photoelectric pulse wave LW(t)) supplied from the photoelectric-pulse-wave detecting device 66.

Then, at SB2, the control device judges whether the pressure in the cuff 10 has been increased up to be equal to, or higher than, a prescribed pressure (e.g., 30 mmHg) because the blood-pressure measurement using the cuff 10 has been started at SA6 of the pressing-condition controlling routine of FIG. 7. This judgment is made for judging whether the pressure pulse wave PW(t) detected by the pressure-pulse-wave sensor 46 is abnormal because the sensor 46 is positioned on the downstream side of the cuff 10 being inflated to press the upper arm 12.

A negative judgment made at SB2 means that the pressure pulse wave PW(t) read in at SB1 is normal. In this case, the control goes to SB3 corresponding to the coefficient determining means 98. At SB3, the control device determines or updates the coefficients of Expression 5 (or Expression 4) representing the relationship R, based on the pressure pulse wave PW(t) and the photoelectric pulse wave LW(t) read in at SB1. Then, at SB4, the pressure pulse wave PW(t) read in at SB1 is displayed on the display device 34, as illustrated in FIG. 5.

Subsequently, at SB5, the control device judges whether the control device has already read in, at SB1 after repetition of the present routine, a length of the pressure pulse wave PW(t) that corresponds to one heartbeat of the patient. If a negative judgment is made at SB5, the control goes back to SB1 and the following steps. Meanwhile, if a positive judgment is made at SB5, then the control goes to SB6 corresponding to the blood-pressure monitoring means 92. At SB6, the control device determines, according to the relationship between blood pressure and magnitude of pressure pulse wave, determined at SA8 of FIG. 7, a monitor diastolic blood-pressure value $MBP_{DIA}$ and a monitor systolic blood-pressure value $MBP_{SYS}$ of the patient, based on a minimal magnitude $PW_{min}$ and a maximal magnitude $PW_{max}$ of the one heartbeat-synchronous pulse of the pressure pulse wave PW(t) read in at SB1, and operates the display device 34 to display the thus determined monitor diastolic and systolic blood-pressure values $MBP_{DIA}$, $MBP_{SYS}$. Then, the control goes back to SB1 and the following steps.

On the other hand, a positive judgment made at SB2 means that the pressure pulse wave PW(t) read in at SB1 is abnormal. In this case, the control goes to SB7 corresponding to the estimated-blood-pressure-waveform determining means 100. At SB7, the control device determines an estimated blood pressure EPW(t−1), based on the photoelectric pulse wave LW(t) read in at SB1 before SB7 in the current control cycle according to the present routine, and based on the current relationship R represented by the above-explained Expression 5 having the coefficients determined or last updated at SB3.

Then, at SB8, the control device operates the display device 34 to display, in place of an image of the pressure pulse wave PW displayed at SB4, an image of the estimated blood-pressure values EPW continuously determined at SB7. Thus, Steps SB2, SB4, and SB8 correspond to the waveform-displaying control means 102.

As is apparent from the foregoing description of the illustrated embodiment, the photoelectric-pulse-wave detecting device 66 is worn on the portion of the patient that is not located on the downstream side of the cuff 10. Therefore, when the cuff 10 is inflated to press the portion around which the cuff 10 is wound, the photoelectric pulse wave LW(t) detected by the photoelectric-pulse-wave detecting device 66 is not influenced by the inflation of the cuff 10. Thus, the estimated blood-pressure waveform EPW (t−1) determined by the estimated-blood-pressure waveform determining means 100 (SB7) based on the photoelectric pulse wave LW8t) detected by the photoelectric-pulse-wave detecting device 66 according to the relationship represented by Expression 5 is not influenced by the inflation of the cuff 10. If the pressure pulse wave PW(t) detected by the pressure-pulse-wave sensor 46 is abnormal, the waveform-displaying control means 102 (SB2, SB6, SB8) operates the display device 34 to display, in place of the pressure pulse wave PW(t), the estimated blood-pressure waveform EPW (t−1) determined by the estimated-blood-pressure waveform determining means 100 (SB7). Thus, the present apparatus 8 can display an accurate blood-pressure waveform even during a blood-pressure measurement.

In addition, the photoelectric-pulse-wave detecting device 66 employed in the illustrated embodiment is small-sized and is light-weighted. Therefore, even if a drip tube may be inserted into the other arm than the arm on which the cuff 10 is worn, the detecting device 66 can be worn on the other arm, without interfering with the drip tube.

Moreover, in the blood-pressure-waveform displaying routine of FIG. 8, the control device 28 (SB2) judges, when the pressure of the cuff 10 is not lower than a prescribed pressure, that the pressure pulse wave PW(t) is abnormal, and operates the display device 34 (SB8) to display the estimated blood-pressure waveform EPW. Therefore, when the pressure pulse wave PW(t) is abnormal because of the inflation of the cuff 10, the estimated blood-pressure waveform EPW is displayed, with reliability, in place of the pressure pulse wave PW(t) being abnormal.

While the present invention has been described in its embodiment by reference to the drawings, it is to be understood that the invention may otherwise be embodied.

For example, in the illustrated embodiment, the photoelectric-pulse-wave detecting device 66 is worn on the end portion 68 of finger of the other arm than the arm around which the cuff 10 is wound. However, the detecting device 66 may be worn on a different portion of the patient, such as a toe or a forehead, so long as the different portion is not located on the downstream side of the cuff 10.

In addition, in the illustrated embodiment, the transmission-type photoelectric-pulse-wave detecting device 66 is employed as the pulse-wave detecting device. However, it is possible to employ, as the pulse-wave detecting device, a reflection-type photoelectric-pulse-wave detecting device; an impedance-pulse-wave sensor which detects, through electrodes, an impedance of an arm or a finger; or a probe for use in an oximeter. Alternatively, in the case where a pressure of a cuff is held at a pressure (e.g., 30 mmHg) in a prescribed pressure range lower than a diastolic blood pressure of a patient, a pressure pulse wave occurs to the cuff. Therefore, a second cuff different from the first cuff 10 for use in blood-pressure measurements may be wound around a portion (e.g., a femoral portion) of a patient that is not located on the downstream side of the cuff 10, and a pulse-wave detecting device which detects a pressure pulse wave occurring to the second cuff may be employed in place of the photoelectric-pulse-wave detecting device 66.

In addition, in the illustrated embodiment, the control device 28 determines, for each of individual patients, the coefficients of Expression 2. However, it is possible to employ, as the coefficients of Expression 1, constant values that are experimentally determined, in advance, to fit a number of patients.

Moreover, in the illustrated embodiment, the relationship represented by Expression 5 based on the ARX model is employed as the predetermined relationship R between estimated blood-pressure waveform EPW and photoelectricpulse-wave LW. However, the relationship R may be represented by a transfer function H with respect to pressure pulse wave PW and photoelectric-pulse-wave LW, defined by the following Expression 6:

$$EPW(t)=H \times LW(t) \quad \text{(Expression 6)}$$

Figure 9:
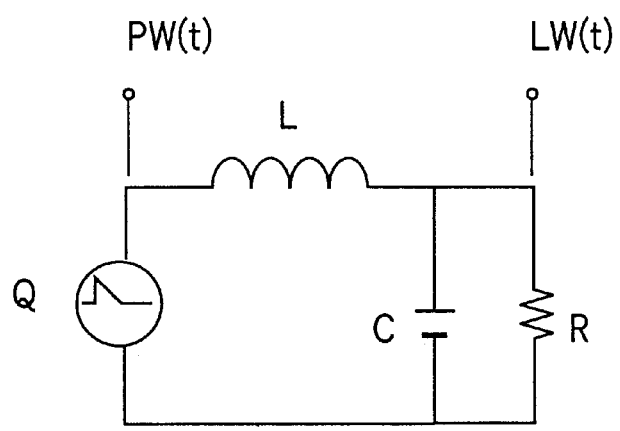
FIG. 9 is a view showing a biological model that is used to determine a transfer function H.

The transfer function H of Expression 6 is determined based on, e.g., Windkessel model, shown in FIG. 9, that models a vascular system. In FIG. 9, symbol "R" indicates a viscous resistance; "C" indicates a compliance of blood vessels of this model; "L" indicates the product of a volume and a density; and "Q" indicates a flow amount of blood.

Alternatively, the predetermined relationship R between estimated blood-pressure waveform EPW and photoelectric-pulse-wave LW may be represented by the following Expression 7 or Expression 8. That is, in an estimated blood-pressure waveform EPW consisting of a number of successive points, an amplitude component and a time component of each of the successive points are determined according to Expression 7 or Expression 8:

$$AEPW(t)=APW(t) \times A' \quad \text{(Expression 7)}$$

In Expression 7, parameter "AEPW(t)" indicates an amplitude component of each of successive points of estimated blood-pressure waveform EPW that are successively determined; "APW(t)" indicates an amplitude component of a point of blood-pressure waveform PW that is detected immediately before blood-pressure waveform PW becomes abnormal; and "A" is an amplitude-correcting coefficient that is successively determined, i.e., a ratio of a magnitude of a peak point of each heartbeat-synchronous pulse of photoelectric pulse wave LW to a magnitude of a peak point of a heartbeat-synchronous pulse of photoelectric pulse wave LW that is detected immediately before blood-pressure waveform PW becomes abnormal.

$$TEPW(t)=TPW(t) \times T' \quad \text{(Expression 8)}$$

In Expression 8, parameter "TEPW(t)" indicates a time component of each of successive points of estimated blood-pressure waveform EPW that are successively determined; "TPW(t)" indicates a time component of a point of blood-pressure waveform PW that is detected immediately before blood-pressure waveform PW becomes abnormal; and "T" is a time-correcting coefficient, i.e., a ratio of a period of each heartbeat-synchronous pulse of photoelectric pulse wave LW to a period of a heartbeat-synchronous pulse of photoelectric pulse wave LW that is detected immediately before blood-pressure waveform PW becomes abnormal.

While the present invention has been described in detail in its embodiment by reference to the drawings, it is to be understood that the present invention is not limited to the described details of the embodiment and may be embodied with various changes and improvements that may occur to a person skilled in the art.

What is claimed is:

1. An apparatus for monitoring a blood-pressure waveform representing a blood pressure of a living subject, comprising:

an inflatable cuff which is adapted to be wound around a first portion of the subject;

a blood-pressure determining device which determines a blood pressure of the subject based on a signal obtained while a pressure in the cuff is changed;

a blood-pressure-waveform detecting device which is adapted to be worn on a second portion of the subject and continuously detects the blood-pressure waveform representing the blood pressure of the subject;

a display device which displays the blood-pressure waveform detected by the blood-pressure-waveform detecting device;

a cuff-using-blood-pressure-measurement starting means for operating, when a prescribed blood-pressure-measurement-starting condition is satisfied, the blood-pressure determining device to determine the blood pressure of the subject;

a pulse-wave detecting device which is adapted to be worn on a third portion of the subject that is not located on a downstream side of the first portion around which the cuff is wound, and which detects a pulse wave from the third portion of the subject;

an estimated-blood-pressure-waveform determining means for continuously determining, based on the pulse wave detected by the pulse-wave detecting device, an estimated blood-pressure waveform representing an estimated blood pressure of the subject, according to a predetermined relationship between blood-pressure waveform and pulse wave; and a waveform-displaying control means for operating, when the blood-pressure waveform detected by the blood-pressure-waveform-detecting device is not abnormal, the display device to display the blood-pressure waveform, and operating, when the blood-pressure waveform is abnormal, the display device to display the estimated blood-pressure waveform in place of the blood-pressure waveform.

2. An apparatus according to claim 1, wherein the pulse-wave detecting device comprises a photoelectric-pulse-wave detecting device which is adapted to be worn on the third portion of the subject, emits a light toward the third portion, and detects a photoelectric pulse wave from the third portion.

3. An apparatus according to claim 1, wherein the waveform-displaying control means judges that the blood-pressure waveform is abnormal, when the pressure of the cuff is not lower than a prescribed lowest pressure at which the cuff would at least partly block a flow of blood through the first portion of the subject, and thereby operates the display device to display the estimated blood-pressure waveform.

4. An apparatus according to claim 2, wherein the photoelectric-pulse-wave detecting device comprises a reflection-type photoelectric-pulse-wave detecting device which detects the photoelectric pulse wave based on the light reflected from the third portion.

5. An apparatus according to claim 2, wherein the photoelectric-pulse-wave detecting device comprises a transmission-type photoelectric-pulse-wave detecting device which detects the photoelectric pulse wave based on the light transmitted through from the third portion.

6. An apparatus according to claim 1, further comprising a relationship determining means for determining the relationship between blood-pressure waveform and pulse wave, based on the blood-pressure waveform detected by the blood-pressure-waveform detecting device and the pulse wave detected by the pulse-wave detecting device.

7. An apparatus according to claim 1, wherein the blood-pressure determining device comprises:

a cuff-pressure changing device which changes the pressure of the cuff;

a cuff-pressure sensor which detects the pressure of the cuff;

a cuff-pulse-wave detecting device which extracts, from the pressure detected by the cuff-pressure sensor, a cuff pulse wave occurring to the cuff while the pressure of the cuff is changed by the cuff-pressure changing device; and a blood-pressure determining means for determining the blood pressure of the subject based on the cuff pulse wave detected by the cuff-pulse-wave detecting device while the pressure of the cuff is changed by the cuff-pressure changing device.

8. An apparatus according to claim 1, wherein the blood-pressure-waveform detecting device comprises:

a pressure-pulse-wave sensor which is adapted to be pressed against an artery of the second portion of the subject via a skin of the second portion, and continuously detects a pressure pulse wave produced from the artery;

a relationship determining means for determining a relationship between blood pressure and pressure pulse wave, based on the blood pressure determined by the blood-pressure determining device and the pressure pulse wave detected by the pressure-pulse-wave sensor; and blood-pressure-waveform determining means for determining, according to the relationship determined by the relationship determining means, the blood-pressure waveform based on the pressure pulse wave detected by the pressure-pulse-wave sensor.

\* \* \* \* \*